United States Patent
Burri et al.

[11] Patent Number: 5,978,090
[45] Date of Patent: Nov. 2, 1999

[54] METHOD AND ARRANGEMENT FOR OPTICAL INSPECTION OF A WELD SEAM

[75] Inventors: Karl-Georg Burri, Oberrieden; Christa Buchmann, Embrach, both of Switzerland

[73] Assignee: Elpatronic AG, Bergdietikon, Switzerland

[21] Appl. No.: 08/940,328

[22] Filed: Sep. 30, 1997

[30] Foreign Application Priority Data

Oct. 10, 1996 [CH] Switzerland ............................. 2469/96

[51] Int. Cl.$^6$ ..................................................... G01B 11/24
[52] U.S. Cl. ........................................... 356/376; 356/237
[58] Field of Search ........................................ 356/376, 390, 356/237; 348/90; 219/124.34, 730.01; 318/577; 901/42, 47, 9

[56] References Cited

U.S. PATENT DOCUMENTS

| | | | |
|---|---|---|---|
| 4,567,348 | 1/1986 | Smith et al. ........................ | 219/124.34 |
| 5,111,126 | 5/1992 | Powell et al. ........................... | 250/216 |
| 5,264,678 | 11/1993 | Powell et al. ........................... | 356/376 |
| 5,572,102 | 11/1996 | Goodfellow et al. .............. | 219/130.01 |

FOREIGN PATENT DOCUMENTS

| | | |
|---|---|---|
| 0532257 | 3/1993 | European Pat. Off. . |
| 0574336 | 12/1993 | European Pat. Off. . |
| 0708325 | 4/1996 | European Pat. Off. . |

*Primary Examiner*—Robert H. Kim
*Attorney, Agent, or Firm*—McCormick, Paulding & Huber

[57] ABSTRACT

In the welding together of sheet-metal blanks an image of a line pattern projected across the weld seam is captured by a camera and evaluated to inspect the weld seam. For improved inspection, a sidewards view of the weld seam is obtained, eg. by means of a prism, in addition to the view from above. This affords an improved and more accurate inspection of the weld seam.

13 Claims, 4 Drawing Sheets

METHOD AND ARRANGEMENT FOR OPTICAL INSPECTION OF A WELD SEAM

BACKGROUND OF THE INVENTION

The invention relates to a method and arrangement for inspecting a weld seam between sheet metal blanks with projected light.

The welding together of sheet-metal blanks to form larger components (so-called tailored blanks), which are subsequently subjected to a forming process, is known. One example of a field in which such tailored blanks are used is the motor vehicle industry. The welding together of the blanks may be performed by mash seam welding or by laser welding. Because the weld seam is subjected to the forming process together with the blanks, it is essential that the entire seam should be of sound quality. The blanks to be welded are fed to the welding station with their joint edges juxtaposed. It is important that the focused laser beam should follow the joint edges of the juxtaposed blanks as accurately as possible. To achieve this, use is made of devices which determine the precise track of the edges ahead of the welding zone, thus enabling the laser beam to be guided accordingly during welding. One known device does this by projecting a line pattern of constant intensity transversely across the edges; this pattern is imaged by a camera, and the image obtained is analysed by computer in order to derive from the trace of at least one of the lines the track of the edges, or as the case may be of the gap, between the blanks at that point. In this way, the edges and the gap are tracked along their entire length ahead of the welding zone and the laser beam is controlled accordingly as welding is performed.

It is also known to employ basically the same method for optically inspecting the weld seam after welding. In this case, one or more lines of light are similarly projected across the weld seam (at right angles to the seam or obliquely), and a camera captures an image of the trace of the projected lines from above. The image obtained is analysed by computer using known image processing methods in order to detect any defects in the seam which disturb the trace of the lines. Depending on the configuration of the seam, differences in thickness between the blanks and their reflectivity, and the nature of any weld defect which may be present, it is possible that the optical weld seam inspection which has been described does not clearly recognise a defect which is present, or that relatively high degree of uncertainty prevails in the analysis as to the existence of a defect.

Therefore the object of the invention is basically to provide an optical inspection of a weld seam which allows better and more certain detection of any weld defects which may occur.

SUMMARY OF THE INVENTION

The present invention resides in a method for inspecting a weld seam resulting from the welding together of sheet-metal blanks along a common edge. Light in the form of at least one line extending transversely across the seam is projected onto the blanks. A view of the weld seam from above is captured by a camera and evaluated, and a sidewards view of the seam area is additionally captured and evaluated.

The invention also resides in an arrangement for inspecting a weld seam resulting from the welding together of sheet-metal blanks along a common edge, and has at least one device for projecting at least one line of light extending transversely across the seam, a camera and an evaluation unit connected thereto. The camera is arranged so as to capture a view of the weld seam from above in the region of the projected line or lines, and a second camera is arranged so as to capture the weld seam from the side in the region of the projected line or lines. Alternately, at least one optical element is provided through which the single camera arranged above the weld seam captures the view from above and also captures a sideward view of the weld seam in the region of the projected line.

By now additionally capturing and analysing a sidewards view of the weld seam area together with the line pattern, the detection of defects can be markedly improved. A full optical inspection of the seam can be obtained. Hitherto this has not been possible, as the steeply inclined regions of the seam were not sufficiently discernible when viewed from above. With the additional sidewards view, defects can be readily detected, even if there is a large difference in thickness between the blanks. Furthermore, seams which appear very dark in the view from above can be analysed better by taking the second view from the side. In general, the result is a more reliable optical quality inspection, irrespective of the geometry of the seam and the thicknesses of the blanks, through the sometimes redundant, evaluation of the views taken from above and from the side.

In one way of carrying out the invention, the sidewards view is captured by a second camera and the images from both cameras are either analysed separately or electronically combined in a single image and analysed together.

In a preferred way of carrying out the invention, however, the view from above and the sidewards view are captured by the same camera, so that both views can easily be analysed sequentially or simultaneously by the same image processing and/or analysing device.

Preferably both views are obtained by means of a single camera which is conventionally positioned vertically above the weld seam and to which the sidewards view is transmitted by at least one optical element such as a prism, a mirror or an optical fibre unit. In a further preferred way of carrying out the invention, the lines of light can also be projected onto the seam by the optical element or elements. It is also possible to use a plurality of lines of different intensities; this can enhance the analysis if there is variation in the reflectivity of the sheet metal surface.

BRIEF DESCRIPTION OF THE DRAWINGS

Embodiments of the invention will now be described in more detail by way of example and with reference to the drawing, in which.

DESCRIPTION OF THE PREFERRED EMBODIMENTS

Figure 1:
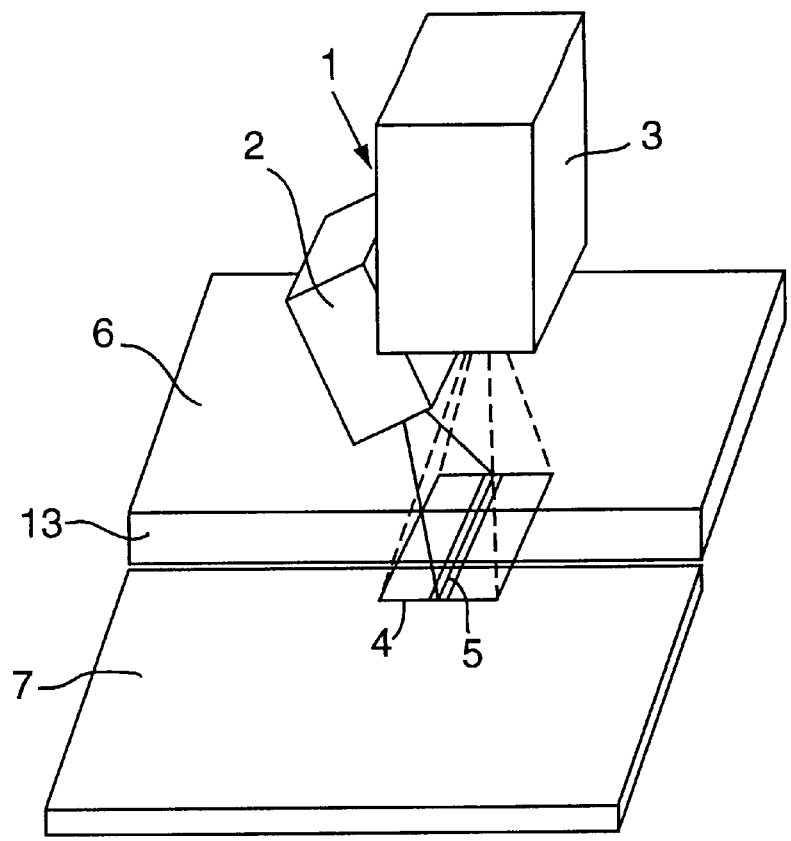
FIG. 1 shows schematically a known arrangement of a camera and line projector for inspecting a weld seam.
Figure 2:
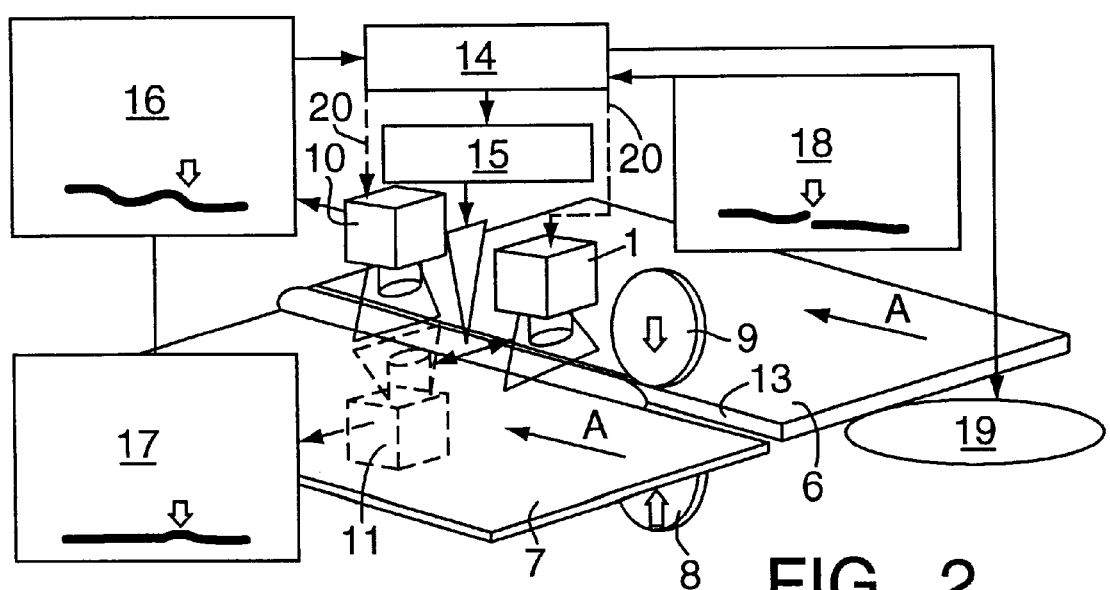
FIG. 2 is a schematic illustration with one edge-following apparatus and two weld seam inspection apparatus.

FIGS. 1 and 2 show two blanks 6 and 7 which are juxtaposed and have a common edge 13. These blanks are joined together along the edge 13 eg. by laser welding. To follow the track of the edge, or, as in the present case, to inspect the weld seam, it is known to project a number of lines 5 of light transversely across the edge 13 onto the said edge and the adjacent region of the two blanks. In the example shown, only three lines are illustrated, but some other number of lines could be employed. The lines extend at a 90° angle to, or at an oblique angle to, the edge 13, within the field of view of an imaging device 3, which may in particular be a CCD camera. The projector 2 for projecting the lines 5 is preferably formed by a laser light source in front of which a diffraction grating is arranged to generate the lines 5 as diffraction lines. The image captured by the camera 3 is analysed in an image evaluation unit in order to determine, from the trace of at least one of the lines 5, the track of the gap between the blanks 6 and 7 along the edge 13, or, as in the present case, the track and condition of the weld seam after the blanks are welded.

FIG. 2 shows such an apparatus in which a number of state-of-the-art optical arrangements as shown in FIG. 1 are provided, namely a first arrangement 1 ahead of the welding zone and two further arrangements 10 and 11 trailing the welding zone. As can be seen from FIG. 2, the blanks 6 and 7, which may be eg. 2m long in the welding direction, are carried through the apparatus in the direction of the arrows A by a conveyor device (not shown) with their position precisely located. A metal reforming device having rollers 8 and 9 may be provided ahead of the edge-following arrangement 1. By deforming the thicker blank 6, this device reduces any gap between the blanks to a minimum. The precise track of the gap is then determined by the edge-following arrangement 1, as already described, by projecting a pattern of lines across the edge 13, and by recording the line pattern by means of a camera and evaluating the pattern. For example, five parallel lines may be projected across the edge by the projection device. The image from the camera of the arrangement 1 passes to an evaluation unit 18 which determines the precise track of the gap. The evaluation unit 18 transmits control signals to a control unit 14, which, in turn, controls the laser light source 15 so that the laser beam (shown only schematically) for welding the blanks 6 and 7 follows exactly the track of the gap along the edge 13.

After the welding zone (ie. in the conveying direction), behind the laser beam, optical arrangements 10 and 11 similar to that shown in FIG. 1 are disposed above the weld seam and underneath the blanks respectively. These two arrangements also project lines across the edge 13, and hence across the weld seam. From the images of the lines, the evaluation units 16 and 17 are able to determine the track of the weld seam and hence to carry out an optical inspection of the weld seam for various kinds of defects, as is known in itself. The evaluation units 16 and 17 transmit an appropriate signal to the control unit 14 and this may transmit a signal to a higher-ranking control 19 to indicate whether the composite panel formed by the welded blanks 6 and 7 satisfies, or fails to satisfy, the quality requirements. Instead of the two evaluation units 16 and 17, one common evaluation unit can of course be provided; or the evaluation may be integrated into the control unit 14.

Figure 3:
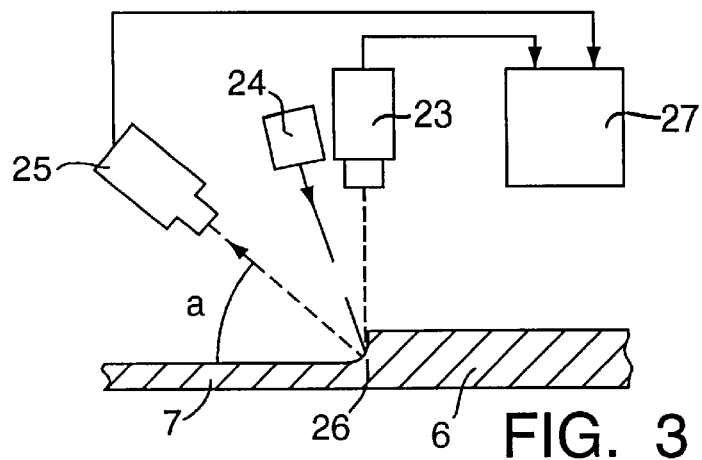
FIG. 3 shows schematically an arrangement according to the invention with two cameras.

In accordance with the present invention, the optical arrangements 10 and 11 enable the weld seam to be viewed not only from above, but also from the side. Such a set-up is illustrated highly schematically in FIG. 3, in which the blanks 6 and 7 are again shown fragmentarily, here being drawn in cross-section, in the welded condition. A first camera 23 and the line projector 24 are arranged above the blanks 6 and 7. Also provided in this embodiment is a second camera 25 which views the seam 26 from the side. The camera 25 is tilted at an angle a of eg. 45° to the blank plane. The images from both cameras are analysed in an evaluation unit 27. The two images of the seam may be electronically combined as a single image for the evaluation. The viewing angle a may be other than 45°, and may lie within a range of eg. 0–85°. The second camera is preferably trained on the same point along the seam as the first camera, and hence on the projected lines of course, the second could also be trained on some other point along the seam, in which case an additional line projector would have to be provided to produce a second pattern of lines at that point. Also, the evaluation would have to take account of the fact that the two images at any instant did not originate from the same point on the seam.

Figure 4:
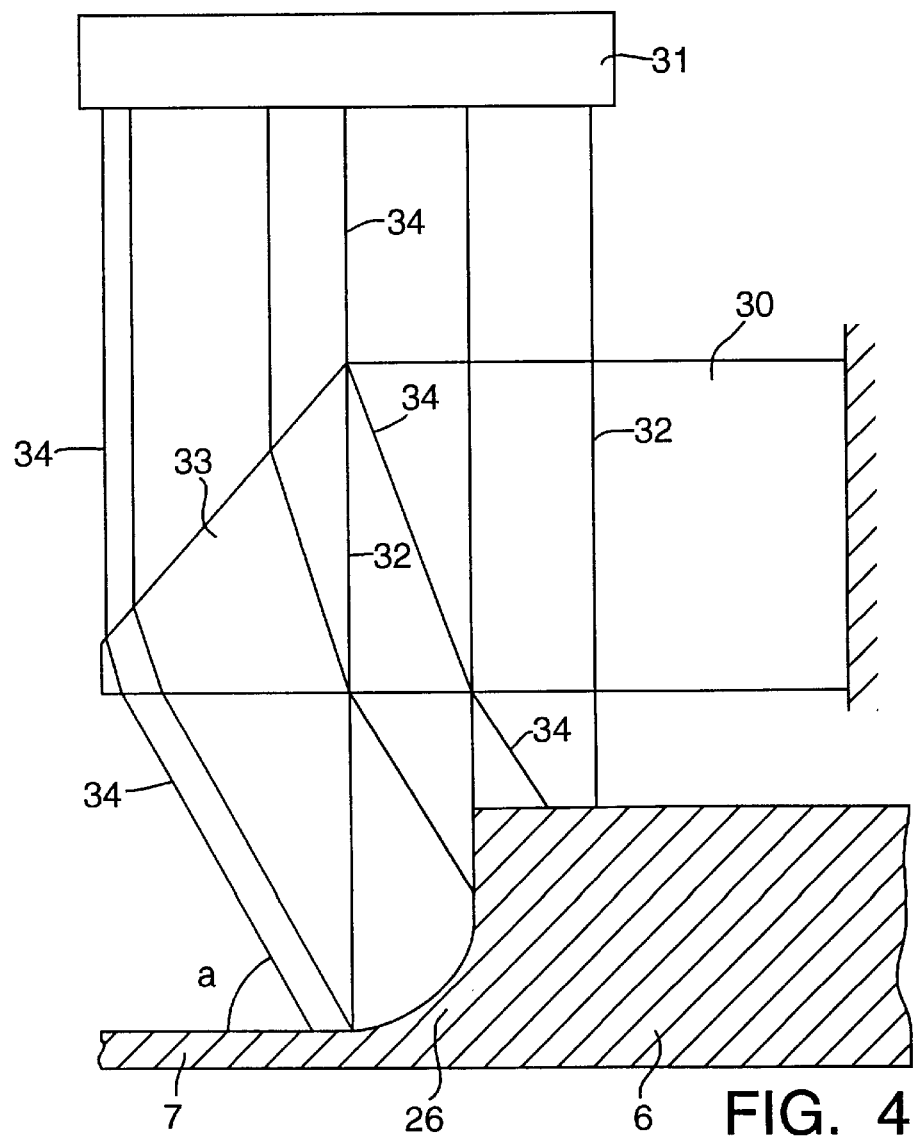
FIG. 4 shows schematically the weld seam area and an optical element for obtaining the sidewards view and the view-from above with a single camera.

FIG. 4 shows a further embodiment in which both views are received by one camera as a single image. The blanks 6 and 7 are again shown only fragmentarily and in cross-section, with 26 denoting the weld seam. An optical element 30, in this case a prism, is placed between the camera 31, shown only schematically as a block, and the blanks 6,7 and has a fixed mounting which is not shown. The line projector is not shown in this illustration. The camera 31 looks vertically downwards through the element 30 onto the seam, and onto the lines projected thereon. This is indicated by the optical path 32. At the same time, the camera 31 views the seam 26 laterally through the sloping face 33 of the optical element 30, at an angle a of approximately 62° (optical path 34). Both views are captured in the same camera image, and can be evaluated together by the evaluation unit (not shown). Here also, it is of course possible to adopt another viewing angle through appropriate configuration of the element.

Figure 5:
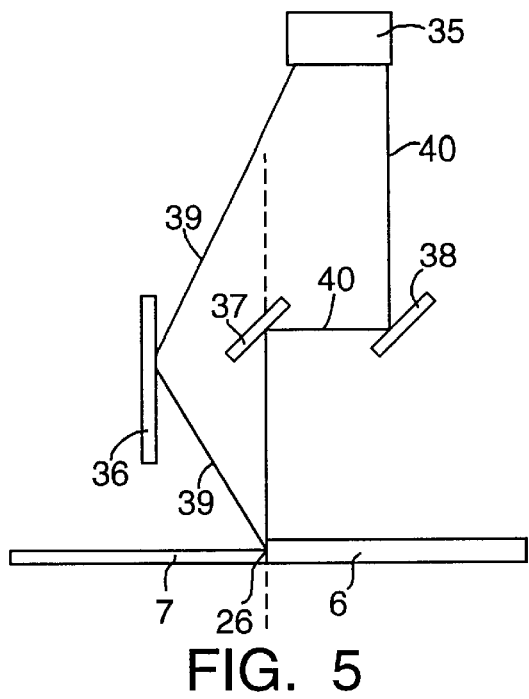
FIG. 5 shows schematically a further embodiment of the invention with optical elements.
Figure 6:
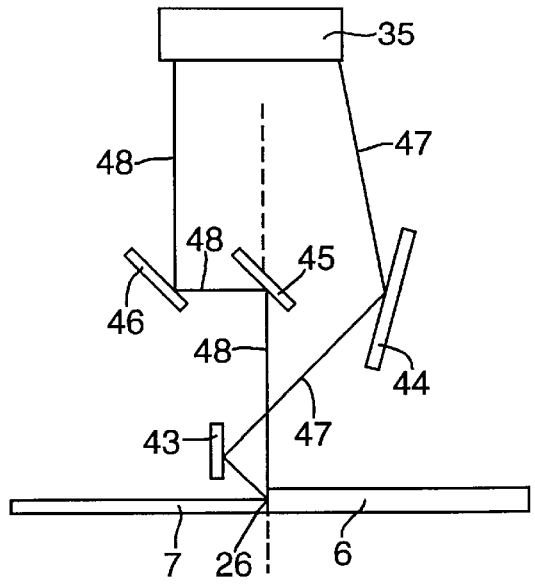
FIG. 6 shows schematically a further embodiment with optical elements.
Figure 7:
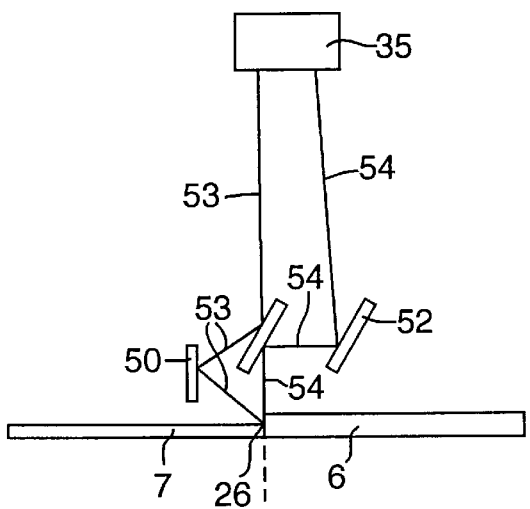
FIG. 7 shows another embodiment with optical elements.
Figure 8:
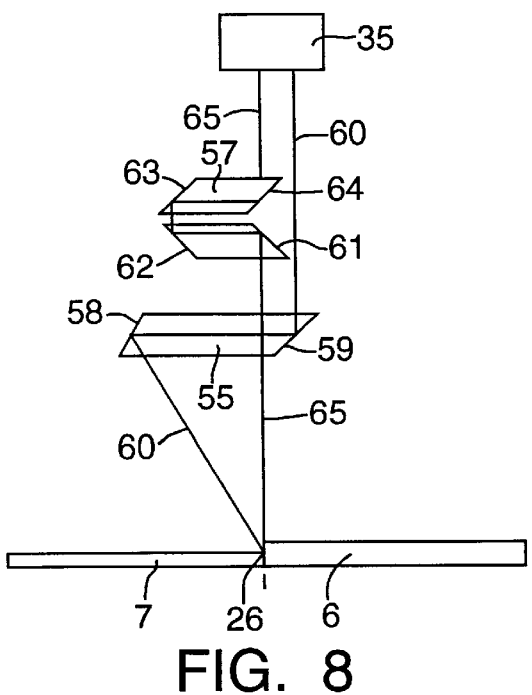
FIG. 8 shows yet another embodiment with optical elements.

FIGS. 5, 6, 7 and 8 also show embodiments each having a single camera 35, with mirrors as optical elements. The line projector and evaluation unit are in each case omitted in order to simplify the drawings. In FIG. 5, one mirror 36 is provided for the sidewards view (optical path 39), and the mirrors 37 and 38 are provided for the view from above (optical path 40). In FIG. 6, the side view of the seam 26 is obtained by mirrors 43 and 44 (optical path 47), and the view from above by the mirrors 45 and 46 (optical path 48). In FIG. 7, the mirror 50 and the mirror 51 (which reflects from both faces) are provided for the sidewards view (optical path 53). The view from above is reflected from the second face of the mirror 51 and the mirror 52 (optical path 54). In FIG. 8 glass blocks 55,56 and 57 with reflecting faces are provided. The sidewards view is then obtained by the reflecting faces 58 and 59 of the block (optical path 60). To obtain a ray path of equal length for the view from above, blocks 56 and 57 are provided with reflecting faces 61–64 (optical path 65).

Figure 9B:
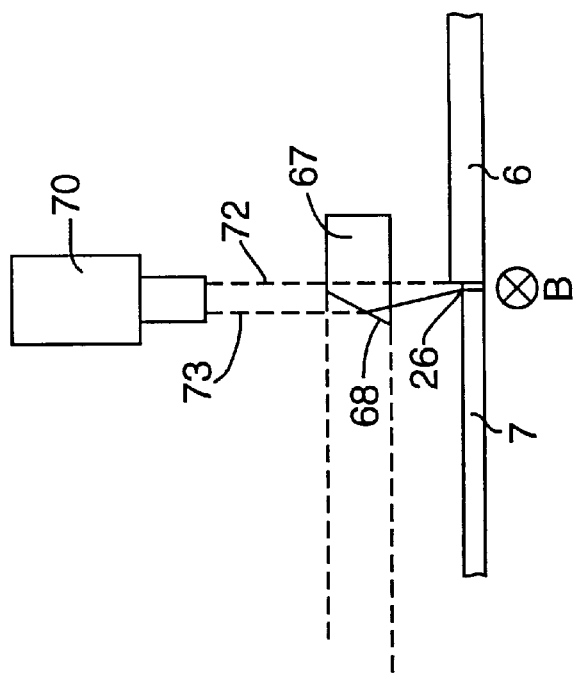
FIG. 9a–9c show an embodiment in which projection of the lines is also performed by means of the optical element.
Figure 9A:
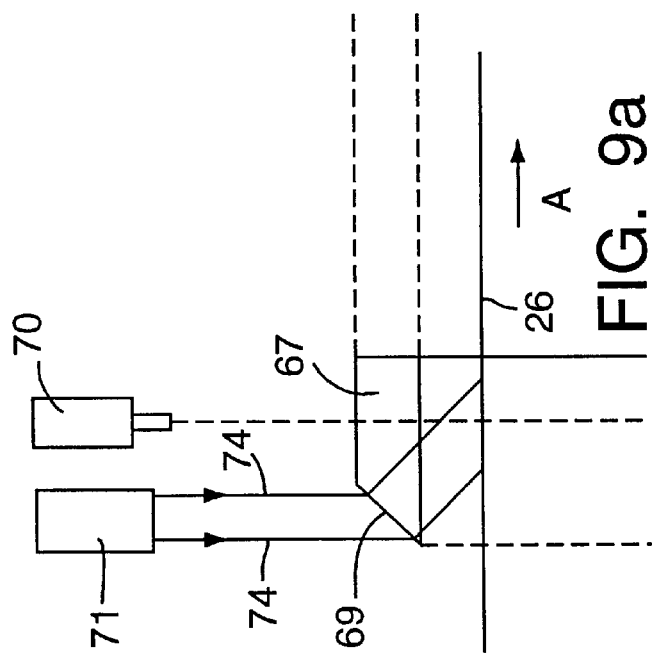
Figure 9C:
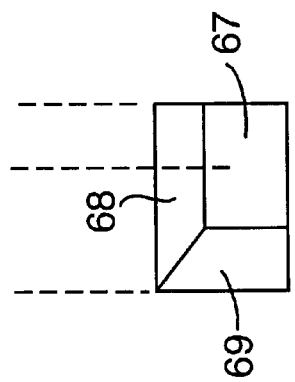

FIGS. 9a to 9c show, in side views from two different sides (FIGS. 9a and 9b) and in top view (FIG. 9c), an embodiment with a prism 67 having two prismatic faces 68 and 69, the light lines again being projected through the prism. A camera 70 is provided, which views the weld seam 26 of the blanks 6,7 from above through the plane face of the prism 67 (optical path 72), and views the seam 26 laterally through the prismatic face 68 (optical path 73) as shown in FIG. 9b, in which the welding direction is perpendicular to the drawing plane as indicated by the arrow B. The line projector 71 projects the lines through the prismatic face 69

(optical path 74) onto the seam 26, so that the lines extend across the seam perpendicularly to the plane of FIG. 9*a* where arrow A indicates the welding direction. FIG. 9*c* shows the corresponding view of the prism 67 from above.

We claim:

1. A method of inspecting a stepped weld seam formed by the welding together of sheet-metal blanks of uneven thickness along a common edge, comprising the steps of:

projecting at least one line of light to extend transversely across said weld seam;

taking a first view of said weld seam and said projected light by means of a camera viewing said seam approximately perpendicularly to the plane of said blanks;

taking a second view of said weld seam and said projected light by means of a camera viewing said seam from the side and facing towards the thicker of said blanks; and evaluating said first and second views of said seam.

2. Method according to claim 1, characterised in that the sidewards view is captured by a second camera and in that the images captured by both cameras are evaluated separately or in a common representation.

3. Method according to claim 1, characterised in that the sidewards view is captured at the same point on the seam, by the same camera and on the same camera image as the view from above, and in that both views are evaluated together.

4. Method according to claim 3, characterised in that at least one optical element, in particular a prism, a mirror or an optical fibre, is provided in order to produce the sidewards view.

5. Method according to claim 4, characterised in that at least one optical element is provided in order to produce the view.

6. Method according to claim 4, characterised in that the line is projected onto the seam through the or at least one optical element.

7. Method according to claim 3, characterised in that at least one optical element, in particular a prism, a mirror or an optical fibre, is provided in order to produce the view from above.

8. Method according to claim 5, characterised in that the line is projected onto the seam through the at least one optical element.

9. Method according to claim 1, characterised in that a plurality of lines of different intensity are projected.

10. Arrangement for inspecting a weld seam from the welding together of sheet-metal blanks along a common edge, comprising at least one device for projecting at least one line of light extending transversely across the seam, a camera and an evaluation unit connected thereto, the camera being positioned so as to capture a view of the weld seam from above in the region of said projected line, characterised in that a second camera is provided which is arranged so as to capture the weld seam from the side in the region of the projected line or lines.

11. Arrangement for inspecting a weld seam resulting from the welding together of sheet-metal blanks along a common edge, comprising at least one device for projecting at least one line of light extending transversely across the seam, a camera and an evaluation unit connected thereto, the camera being positioned so as to capture a view of the weld seam from above in the region of the projected line or lines, characterised in that at least one optical element is provided through which the camera arranged above the weld seam to capture the view from above also captures a sidewards view of the weld seam in the region of the projected line or lines.

12. Arrangement according to claim 11, characterised in that a prism, a mirror or an optical fibre is provided as optical element.

13. Arrangement according to claim 11, characterised in that the line projector and the optical element or at least one optical element are arranged so that the line or lines can be projected through the optical element onto the seam area.

* * * * *